United States Patent [19]

Wilson et al.

[11] Patent Number: 5,496,846
[45] Date of Patent: Mar. 5, 1996

[54] TAXOL TREATMENT OF BREAST CANCER

[75] Inventors: Wyndham H. Wilson; Robert Wittes, both of Washington, D.C.

[73] Assignee: The United States of America as represented by the Department of Health and Human Services, Washington, D.C.

[21] Appl. No.: 178,463

[22] Filed: Jan. 6, 1994

Related U.S. Application Data

[63] Continuation of Ser. No. 950,380, Sep. 22, 1992.

[51] Int. Cl.$^6$ ................................................ A61K 31/335
[52] U.S. Cl. ................................................ 514/449
[58] Field of Search ................................................ 514/449

[56] References Cited

PUBLICATIONS

Holmes, F. A., et al., "Phase II Trail of Taxol, an Active Drug in the Treatment of Metastatic Breast Cancer", J. Natl. Cancer Inst., 83, No. 24, 1797–1805 (Dec. 18, 1991).

Extra, J. M., et al., "Phase I Trial of Taxotere", Proc. Am. Assoc. Cancer Res. Annu. Meet., 32, 205, (Mar. 1991).

Schmid, S. M., et al., "IFN 6 Augmentation of Taxol Anticellular Effect: Comparison with Taxol/Cisplatin or Taxol/Adriamycin in MCF–7 Breast Carcinoma Cells", J. Interferon Res. 11 (Suppl. 1) S237 (1991).

Fojo, A. T., et al., "Expression of A Multidrug–Resistance Gene in Human Tumors and Tissues", Proc. Natl. Acad. Sci. USA 84, 265–269, (Jan. 1987).

Rowinsky et al., Cancer Research, vol. 49, No. 16, pp. 4640–4647, Aug. 15, 1989.

*Primary Examiner*—Jerome D. Goldberg
*Attorney, Agent, or Firm*—Morgan & Finnegan

[57] ABSTRACT

The present invention is a method of treatment for a patient with cancer. In particular, it is a method of treating patients having breast cancer using the microtubule agent, Taxol. The present method of administration, serves to prevent or retard the adverse side effects associated with Taxol and reduces the chances of a patient developing mdr Taxol resistance. The novel method of treatment provides a low-dose, long-term exposure to Taxol in a patient.

1 Claim, No Drawings

TAXOL TREATMENT OF BREAST CANCER

This is a continuation of U.S. application Ser. No. 07/950,380, filed on Sep. 22, 1992.

FIELD OF THE INVENTION

The present invention relates to a method of treating patients who have breast cancer.

More particularly, the invention relates to treatment of patients with a taxol solution administered as a 96 hour continuous infusion every 21 days.

BACKGROUND OF THE INVENTION

Taxol is a microtubule agent isolated from the stem bark of *Taxus brevifolia*, the western (Pacific) yew tree. Taxol acts by promoting the formation of unusually stable microtubules, inhibiting the normal dynamic reorganization of the microtubule network required for mitosis and cell proliferation (Schiff, P. B., et al. (1979) *Nature* 277, 665; Schiff, P. B., et al. (1981) *Biochemistry* 20, 3247). In the presence of Taxol, the concentration of tubulin required for polymerization is significantly lowered; microtubule assembly occurs without GTP and at low temperatures, and the microtubules formed are more stable to depolymerization by dilution, calcium, cold, and inhibitory drugs. Taxol will reversibly bind to polymerized tubulin, and other tubulin-binding drugs will still bind to tubulin even in the presence of Taxol.

Taxol interacts with the microtubule system of many types of organisms. For example, in mammalian cells a 50 Nm Taxol concentration usually causes a significant increase in microtubule number, with changes in cell shape and mitotic arrest in actively dividing cells. (Parness, J., et al. (1982) *Biochem. Biophys. Res. Commun.* 105, 1082). These perturbations of microtubule function caused by Taxol have a critical impact on the cell because of the role played by microtubules in cell motility, secretion, and cell division.

Taxol has been studied for its effect in combating tumor growth in several clinical trials using a variety of administration schedules. Severe allergic reactions have been observed following administration of Taxol. However, it has been demonstrated that the incidence and severity of allergic reactions is affected by the rate of Taxol infusion (Weiss, R. B., et al. (1990) *J. Clin. Oncol.* 8, 1263).

Cardiac arrhythmias are associated with Taxol administration, and like allergic reactions, their incidence is affected by the rate of Taxol administration. Sinus bradycardia and Mobitz II arrhythmia will develop in approximately 40% and 5% of patients, respectively, beginning 4–6 hours after the start of a Taxol infusion, and continuing for 4–8 hours after its completion. In most patients, the abnormal rhythm is hemodynamically stable and does not require cardiac medications. Additionally, it has been observed that the incidence of severe cardiac events is low in patients receiving Taxol alone. Thus, infusion times up to 24 hours have been used in treatment with Taxol to decrease the incidence of toxicity and allergic reaction to the drug. Data from these studies indicates that reversible myelosuppression is the dose limiting toxicity, with significant peripheral neuropathy observed at doses of 275 mg/M$^2$ and greater. Other toxicities include myalgia, mucositis, and alopecia.

Clinical studies of Taxol have been performed in a number of tumors including acute leukemias, breast cancer, ovarian cancer and melanoma. In one study of 34 patients with ovarian cancer treated with 250 mg/M$^2$ Taxol as a 24 hour continuous infusion, there was a 21% objective response rate (Enzig, A. I. (1990) *Proc. AACR* 31, 187). The major toxicities were neutropenia and peripheral neuropathy. Another study of 30 patients with melanoma treated with the same dose and schedule of Taxol exhibited an objective response rate of 13% (Enzig, A. I. (1988) *Proc. ASCO* 7, 249).

Rowinsky, E. K., et al. ((1989) *Cancer Res.* 49, 4640) describes a phase I study of Taxol in 17 patients with refractory acute leukemia. Taxol was administered as a 24 hour continuous infusion and escalated from 200 to 390 mg/M$^2$. Severe mucositis limited further dose escalation, and other nonhematological effects included peripheral neuropathy, alopecia, myalgias, arthralgias, nausea, vomiting, and diarrhea. Based on this study, the maximum tolerated dose and recommended phase II doses for Taxol were 390 and 315 mg/M$^2$, respectively. Nine patients had transient reductions in peripheral blood and bone marrow blasts, and three patients had complete clearance of leukemia for less than one month.

Two mechanisms of Taxol resistance have been identified in vitro. In one type of cell, resistance is on the basis of drug efflux, and like other multidrug-resistant (mdr) cell lines, it has increased levels of membrane P-glycoproteins(s), and shows increased drug efflux (Gupta, R. S. (1985) *Cancer Treat. Rep.* 69, 515). These cells are also resistant to the vinca alkaloids, doxorubicin, and other natural products, and resistance is reversible with calcium channel blockers such as verapamil (Racker, E., et al. (1986) *Cancer Treat. Rep.* 70, 275). Another mechanism of resistance found in other taxol-resistant cells involves mutations in the alpha- or beta-tubulin subunits, with some of these cell lines actually requiring taxol for growth and mitotic spindle formation (Schibler, M. J., et al. (1986) *J. Cell Biol.* 102, 1522).

A potentially important factor in the area of Taxol research involves the multidrug resistant gene (mdr). The product of this gene, called the p170 glycoprotein, has been demonstrated in vitro to play a role in resistance of tumor cells to Taxol. It has been demonstrated that p170 functions as a membrane pump which actively transports intracellular drug out of the cell. Using in vitro cell models, several classes of drugs have been identified which block the action of p170, including cyclosporin A, calcium channel blockers, phenothiazines, and anti-arrhythmic drugs such as quinidine and amiodarone. These drugs have been shown to reverse mdr-induced drug resistance by increasing intracellular drug concentrations.

Investigators have found increased expression of mdr in a variety of tumor types, including lymphoma and breast cancer. For example, Goldstein, L. J., et al. ((1989) *J. Nat'l Com. Inst.* 81, 116) reports moderately increased mdr expression in 22% (4/18) of untreated lymphomas and in 60% (3/5) of treated lymphomas. Although it is unknown if increased mdr expression is a clinically relevant mechanism of drug resistance, there is in vitro evidence that mdr plays a role in drug resistance to Taxol.

Although it is clinically unknown whether Taxol, an antimicrotubule agent effective in the treatment of cancer, is less effective in cells expressing the mdr gene, in vitro data shows that this is a concern. Furthermore, no one has been able to demonstrate an effective regimen for treatment of lymphomas and breast cancer which overcomes the problem of mdr drug resistance. The present invention discloses a method of treating breast cancer with a low-dose long term exposure to Taxol. There is clinical and laboratory evidence that long infusion times, on the order of 72–96 hours, may enhance the activity of drugs, such as Taxol, which are transported by P-glycoprotein. (Lai, G. M., et al. (1991) *Int. J. Cancer*, 49, 696). Thus the method of the present invention is to administer taxol as a 96 hour infusion in patients with breast cancer, to effectively treat the disease and potentially reduce the chances of developing mdr Taxol resistance.

Accordingly, an object of this invention is to provide a method of Taxol treatment effective against breast cancer.

An additional object of this invention is to provide a method of Taxol treatment which reduces or eliminates the development of mdr Taxol resistance.

SUMMARY OF INVENTION

In accordance with these and other objects of the present invention, a method of treating breast cancer with Taxol, with a reduced chance of developing mdr Taxol resistances is provided which comprises administration of Taxol as a 96 hour continuous infusion with a dose level of between 70 and 140 mg/M$^2$/96 hours, the dose level being dependent on the toxicity of Taxol on the patient.

This method provides an effective way of treating breast cancer with Taxol. Additionally, because of the low-dose prolonged exposure regimen, the chance of a patient developing mdr Taxol resistance and other adverse reactions is potentially reduced.

DETAILED DESCRIPTION OF THE INVENTION

For the practice of one embodiment of the present invention one must first prepare the Taxol solution. Taxol is supplied through CTEP, DCT, NCI (IND#22850) as a concentrated solution, 6 mg/ml, in 5 ml vials (30 mg/vial) in a polyoxyethylated castor oil (Cremophor EL®) 50% and dehydrated alcohol, USP (50%) vehicle. The intact vials should be stored under refrigeration and diluted prior to use. When diluted in either 5% Dextrose Injection or 0.9% Sodium Chloride, Taxol concentrations of 0.3–1.2 mg/ml are physically and chemically stable for at least 12 hours at room temperature. (NCI Investigational Drugs; Pharmaceutical Data (1990)). It has also been demonstrated that Taxol concentrations of 0.6 mg/ml diluted in either D5W or NS and 1.2 mg/ml diluted in NS prepared in polyolefin containers are stable for at least 25 hours at ambient temperatures (20°–23° C.). (Waugh, et al. (1990) *Am. J. Hosp. Pharm.* 48, 1520).

All solutions of Taxol exhibit a slight haziness directly proportional to the concentrations of drug and time elapsed after preparation. Formulation of a small number of fibers in the solution (within acceptable limits established by the USP Particulate Matter Test for LVP's) has been observed after preparation of Taxol infusion solutions. While particulate formation does not indicate loss of drug potency, solutions exhibiting excessive particulate matter formation should not be used. Therefore, in-line filtration may be necessary and can be accomplished by incorporating a hydrophilic, microporous filter with a pore size no greater than 0.22 microns (IVEX-HP In Line Filter Set-SL, 15", Abbott model #4525 or equivalent) into the fluid pathway distal to the infusion pump.

Taxol must be prepared in non plasticized solution containers (e.g., glass, polyolefin, or polypropylene) due to leaching of diethylhexylphthlalate (DEHP) plasticizer from polyvinyl chloride (PVC) bags and intravenous tubing. Taxol must not be administered through PVC intravenous sets. Therefore, polyolefin- or polyethylene-line sets, such as IV nitroglycerin sets (or equivalent) should be used to connect the bottle or bag (containing the Taxol infusion solution) to the IV pump, a 0.22 micron filter is then attached to the IV set, and then may be directly attached to the patient's central access device. If necessary, a polyolefin-line extension set (Polyfin™ Extension Set, MiniMed Technologies, Model #126) can be used to provide additional distance between the IV pump and the patient's central access device.

To practice the invention, the final infusion solution may be prepared by diluting the total daily Taxol dose (i.e., a 24 hour supply) in 250 or 500 ml of 5% Dextrose Injection, USP or 0.9% Sodium Chloride Injection, USP in either a glass, polyolefin or polypropylene container. Each bottle will be infused over 24 hours via an infusion control device. A total of four (4) bags/bottles are required for each 96 hour infusion. Each bottle should be prepared immediately prior to use such that no more than 25 hours will elapse from the time of preparation until the end of the infusion for each bag/bottle. As described above, a polyolefin- or polyethylene-line set should be used to connect the bag/bottle to the IV pump, followed by the in-line filter which will be directly attached to the patient's central access device.

The method of an embodiment of the present invention involves administration of Taxol infusion solution as a 96 hour continuous intravenous infusion. The Taxol solution is delivered through a permanent central intravenous catheter, with cycles repeated every 21 days. Therefore, before starting the therapy, patients must have a permanent or temporary central venous access.

Because of the possibility of anaphylactoid reactions, a physician should be readily available during the first 30 minutes of each infusion, and IV epinephrine, hydrocortisone, and diphenhydramine should also be kept available. However, because of the prolonged 96 hour infusion, a very low incidence of reactions is anticipated.

The following example illustrates a preferred embodiment of the present invention, but should not be used to limit its scope.

EXAMPLE

The following criteria are used to measure the response to Taxol treatment using an embodiment of the present invention:

Partial Remission (PR): Greater than 50% decrease in the sum of the products of the diameters of all measurable lesions for at least one month.

Minor Remission (MR): 25 to 50% decrease in the sum of the products of the diameters of all measurable lesions for at least one month.

Progressive Disease (PD): 25% or greater progression in the sum of the products of the diameter of any measurable lesion over one cycle of chemotherapy or the appearance or any new lesion consistent with metastatic disease.

Taxol was obtained as a concentrated solution, 6 mg/ml, in 5 ml vials (30 mg/vial) in 50% polyoxyethylated castor oil and 50% dehydrated alcohol. The Taxol was then diluted in 500 ml 5% Dextrose, to a concentration sufficient to supply between 17.5 and 35 mg of Taxol per square meter (based on the body surface area of the patient) over a 24 hour period. The Taxol infusion preparation was prepared between 30 and 60 minutes prior to beginning each 24 hour infusion. The Taxol infusion solution was prepared in a polypropylene lined semi-rigid container, in a volume of 500 ml.

The container [bag] with the Taxol infusion solution was connected to an IV pump via a polyethylene tube An IVEX-HP In Line Filter Set-SL, 15", Abbott model #4525 with a pore size of 0.22 microns was then attached to the IV pump via a polyethylene line-tubing. The in-line filter was then connected to the subjects central access device.

The Taxol solution was infused over a 24 hour period, controlled by the IV pump. The procedure was repeated three more times, for a total 96 hour continuous infusion. The final dose was between 70 and 140 mg/M$^2$/96 hours.

Twenty-three patients (11 breast, 2 Hodgkin's disease (HD), 4 mycosis fungoides (MF) and 6 non-Hodgkin's lymphoma (NHL)) were treated with the Taxol solution at the above-described rate of between 70 and 140 mg/M$^2$/96 hrs. This 96 hr continuous infusion was repeated every 21 days, while patients were monitored for a response after every two cycles. If a patient exhibited a toxic or allergic reaction to a dose of Taxol, the dosage was lowered until tolerated. The cycles were continued until a patient exhibited disease progression or was stable for 4–6 cycles. All breast cancer patients had received a doxorubicin or mitoxantrone containing regimen for metastatic disease. Seven of these patients failed to respond, while the other four responded but did not achieve complete remission. All of the lymphoma patients failed to respond to multiple regimens within 6 months of receiving Taxol.

After treatment of the patients with the above-described Taxol infusion solution at a rate of between 70 and 140 mg/M$^2$/96 hrs, every 21 days, patients were observed for response after every two cycles. In the breast cancer group, 9 out of the 11 patients exhibited a positive response (7 PR, 2 MR) to the treatment, for a 82% total response rate. The seven of eleven (64%) partial remission rate achieved in breast cancer patients is highly favorable over the 33% response rate reported for a 24 hour infusion at 250 mg/M$^2$ in a similar patient group. (Holmes, F. A., et al. (1991) *Int'l Nat'l Cancer Inst.* 83, 1797).

Among the lymphoma patients treated, Taxol was active in 4 out of 6 patients (3 PR, 1 MR) with diffuse large cell lymphoma. No prior treatment of lymphoma with Taxol has been reported. The 50% partial remission rate is favorable compared to the response rates determined for Taxol treatment of other cancer types.

The invention has been described in detail with particular reference to a preferred embodiment thereof, but it will be understood that the invention is capable of other and different embodiments. As is readily apparent to those skilled in the art, variations and modifications can be affected within the spirit and scope of the invention. Accordingly, the foregoing disclosure and description are for illustrative purposes only, and do not in any way limit the invention, which is defined only by the claims.

We claim:

1. A method of treating a patient suffering from breast cancer, which comprises:
   (a) intravenously infusing taxol into said patient at a continuous dosage rate of between 17.5 to 35 milligrams of taxol per square meter of patient surface area per 24 hours to infuse between 70 and 140 milligrams of taxol per square meter of patient surface area into said patient over a period of 96 hours; and
   (b) repeating said step (a) in 21 day cycles until remission of said patient's breast cancer is obtained.

* * * * *